United States Patent
Sato

(10) Patent No.: US 10,667,792 B2
(45) Date of Patent: Jun. 2, 2020

(54) ULTRASONIC DIAGNOSTIC APPARATUS, ULTRASONIC IMAGE PROCESSING APPARATUS AND ULTRASONIC DIAGNOSTIC APPARATUS CONTROL METHOD

(71) Applicant: Toshiba Medical Systems Corporation, Otawara-shi (JP)

(72) Inventor: Takeshi Sato, Nasushiobara (JP)

(73) Assignee: Canon Medical Systems Corporation, Otawara-shi (JP)

( * ) Notice: Subject to any disclaimer, the term of this patent is extended or adjusted under 35 U.S.C. 154(b) by 1227 days.

(21) Appl. No.: 14/869,032

(22) Filed: Sep. 29, 2015

(65) Prior Publication Data

US 2016/0089115 A1 Mar. 31, 2016

(30) Foreign Application Priority Data

Sep. 30, 2014 (JP) .................................. 2014-201730

(51) Int. Cl.
*A61B 8/08* (2006.01)
*A61B 8/06* (2006.01)
*A61B 8/14* (2006.01)

(52) U.S. Cl.
CPC .............. *A61B 8/5207* (2013.01); *A61B 8/06* (2013.01); *A61B 8/5223* (2013.01); *A61B 8/145* (2013.01); *A61B 8/488* (2013.01)

(58) Field of Classification Search
CPC ........... A61B 8/06; A61B 8/145; A61B 8/488; A61B 8/5207; A61B 8/5223
See application file for complete search history.

(56) References Cited

U.S. PATENT DOCUMENTS

2005/0148875 A1    7/2005  Sato
2007/0038091 A1*   2/2007  Shiki .................. A61B 8/06
                                                    600/437

(Continued)

FOREIGN PATENT DOCUMENTS

JP    2005-176997 A    7/2005
JP    3724846          12/2005

(Continued)

OTHER PUBLICATIONS

Steinar Bjaerum et al. "Clutter Filters Adapted to Tissue Motion in Ultrasound Color Flow Imaging", IEEE Transactions on Ultrasonics, Ferroelectrics, and Frequency Control, vol. 49, No. 6, Jun. 2002, 12 pages.

*Primary Examiner* — Amelie R Davis
(74) *Attorney, Agent, or Firm* — Oblon, McClelland, Maier & Neustadt, L.L.P.

(57) ABSTRACT

An ultrasonic diagnostic apparatus according to an embodiment performs ultrasonic scans having a plurality of times of ultrasonic transmission and reception as a basic unit, and acquires reception signals respectively for reception rasters allocated with respect to a predetermined region of a subject. The apparatus generates first signals corresponding to the reception rasters respectively by performing adding processing or low-pass filtering having a time of the ultrasonic scan as a unit with respect to the reception signals respectively acquired for the reception rasters, and acquires power information of a moving body in the predetermined region based on a second signal to be obtained by performing an MTI filtering with respect to the first signals. The apparatus acquires velocity information of the moving body based on a third signal obtained by performing the MTI filtering with respect to the reception signals respectively acquired for the reception rasters.

19 Claims, 12 Drawing Sheets

(56) References Cited

U.S. PATENT DOCUMENTS

2007/0239015 A1 10/2007 Sato
2015/0320395 A1 11/2015 Sato

FOREIGN PATENT DOCUMENTS

| JP | 4928801 B2 | 5/2012 |
| JP | 2014-158698 A | 9/2014 |
| WO | WO 2014/021402 A1 | 2/2014 |

\* cited by examiner

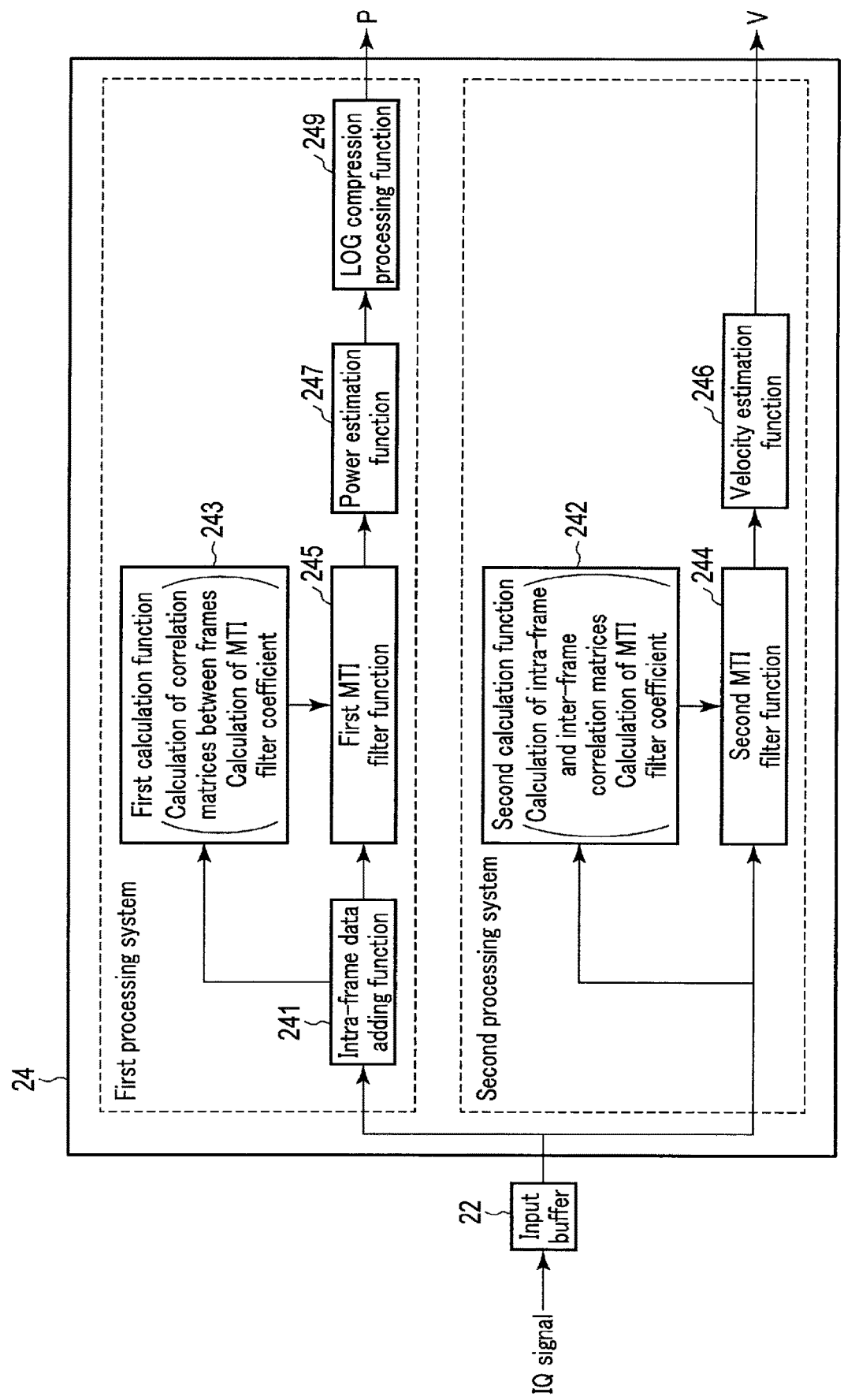
F I G. 2

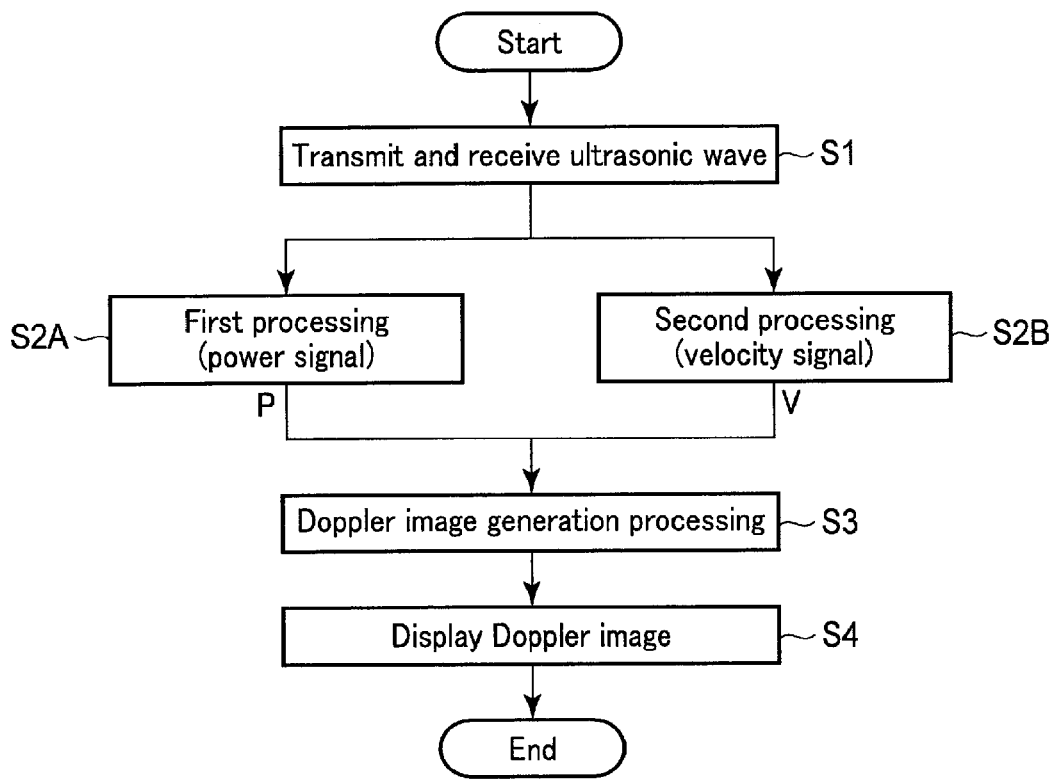
F I G. 3

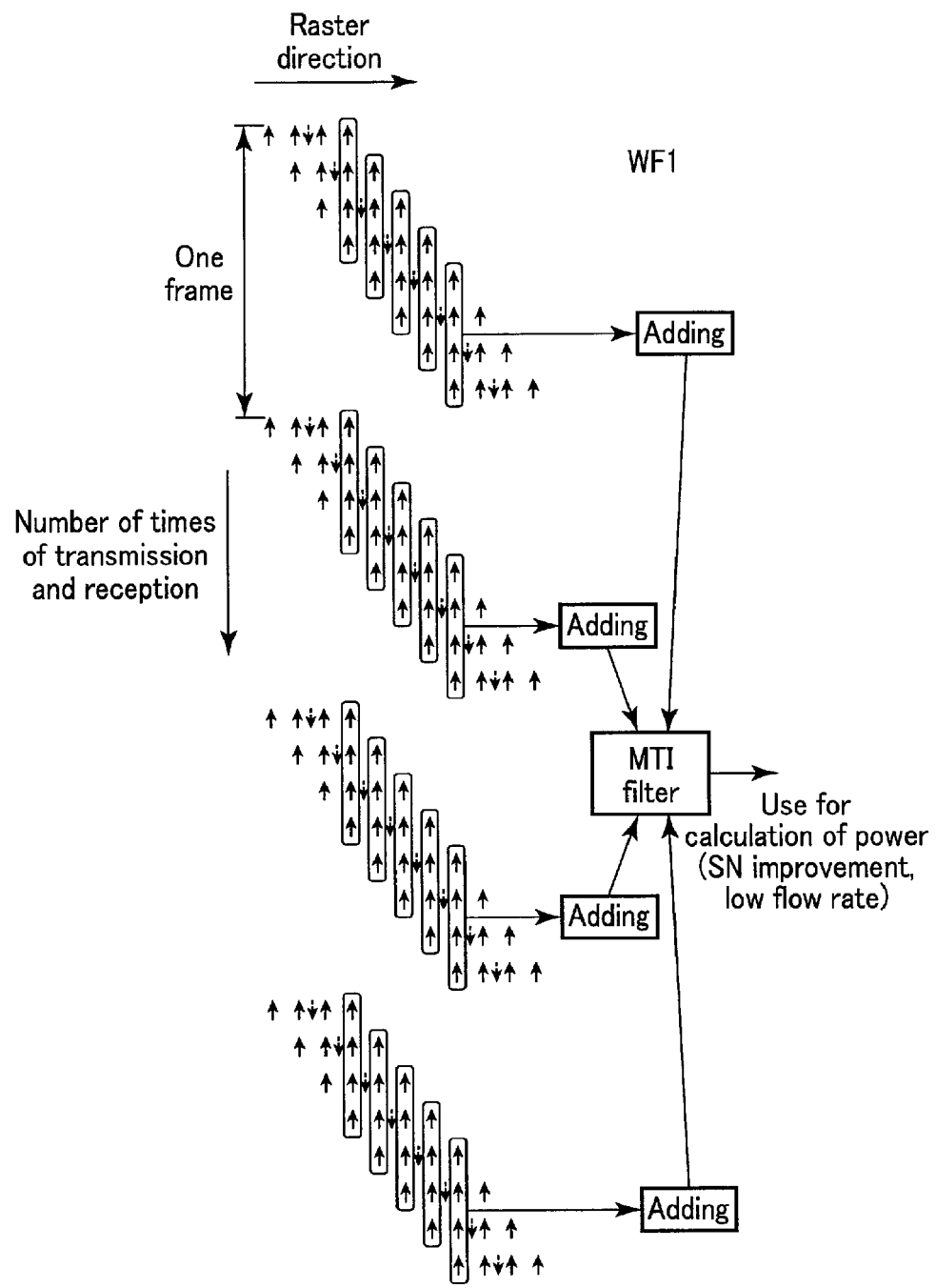
F I G. 5A

ULTRASONIC DIAGNOSTIC APPARATUS, ULTRASONIC IMAGE PROCESSING APPARATUS AND ULTRASONIC DIAGNOSTIC APPARATUS CONTROL METHOD

CROSS-REFERENCE TO RELATED APPLICATIONS

This application is based upon and claims the benefit of priority from the Japanese Patent Application No. 2014-201730, Sep. 30, 2014, the entire contents of all of which are incorporated herein by reference.

FIELD

This embodiment relates to an ultrasonic diagnostic apparatus, an ultrasonic image processing apparatus and an ultrasonic diagnostic apparatus control method that implements a high aliasing velocity, an excellent low flow rate detectability, and a high sensitivity in ultrasonic diagnosis that images a blood flow or a moving object.

An ultrasonic diagnostic apparatus can display a pulsation of a heart and a state of a fetus' motion in real time with a simple operation by bringing an ultrasonic probe into contact with a body surface, and further, has a high safety and thus, it is possible to repeatedly perform examinations. Besides, the ultrasonic diagnostic apparatus has a small system scale as compared to another diagnostic equipment using such as X-ray, computerized tomography (CT) and magnetic resonance imaging (MRI), and is capable of easily performing examination by being moved to a bedside, which can be referred to as a convenient diagnosis method. Although there are various types of ultrasonic diagnostic apparatuses to be used in such an ultrasonic diagnosis depending on types of functions provided in the respective apparatuses, and among them, a small apparatus having a size that can be carried with one hand has been developed, and the ultrasonic diagnosis does not cause exposure to radiation unlike the X-ray and the like, and thus, can be used in obstetrics, home medical care and the like.

It is possible to image the moving object such as the blood flow and a contrast agent by an imaging method called a color Doppler or power Doppler method using such an ultrasonic diagnostic apparatus. In such a Doppler imaging method, a method is generally performed in which a plurality of times of transmission and reception are performed in the same direction, a moving target indicator (MTI) filter is applied with respect to a data string thereof, and only a set of velocity, dispersion, power of the blood flow is output and displayed. Since a frame rate decreases with such a method, a method of improving the frame rate by using data between frames has been developed. Further, in a case where the blood flow data is used between frames, there occurs a problem that an aliasing velocity decreases, but a method of avoiding such a problem by applying the MTI filter with respect to an unequally spaced data string has been also developed.

However, the above-described MTI filter with respect to the unequally spaced data string is a filter with a fixed coefficient. Thus, there is a problem that motion artifact is easily generated without being capable of coping with a motion of the living body that constantly changes due to heartbeat and breathing. Further, when a minute blood flow is observed according to the conventional technique, a signal-to-noise ratio (S/N) of a signal becomes a problem in addition to the low flow rate detectability.

From a viewpoint of the above-described situation, an object is to provide an ultrasonic diagnostic apparatus, an ultrasonic image processing apparatus and an ultrasonic diagnostic apparatus control method having a high aliasing velocity and a high low flow rate detectability, and capable of imaging a blood flow or a moving object with a high frame rate, and a high S/N.

BRIEF DESCRIPTION OF THE DRAWINGS

FIG. 2 is a functional block diagram of a color Doppler processing circuit 24 of the ultrasonic diagnostic apparatus according to the embodiment;

FIG. 3 is a flowchart illustrating a flow of a process implemented in Doppler imaging of the ultrasonic diagnostic apparatus according to the embodiment;

FIGS. 5A and 5B are diagrams for describing signal processing to be performed in a first processing system and a second processing system of the color Doppler processing circuit 24;

DETAILED DESCRIPTION

Figure 1:
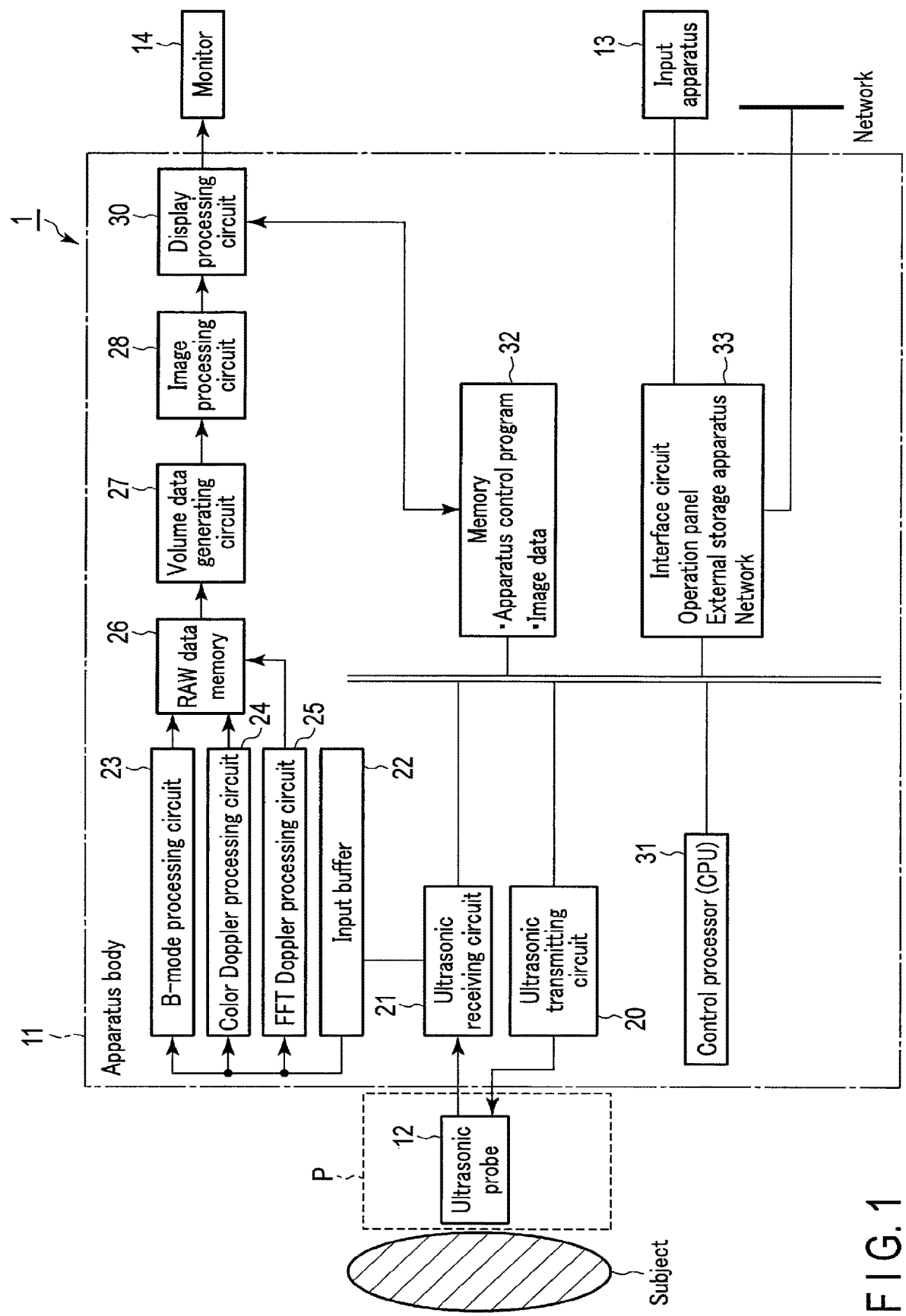
FIG. 1 is a block diagram illustrating a configuration of an ultrasonic diagnostic apparatus according to an embodiment.

An ultrasonic diagnostic apparatus according to an embodiment is provided with reception signal acquisition circuitry, power information acquisition circuitry, velocity information acquisition circuitry and image generating circuitry. The reception signal acquisition circuitry performs a plurality of times of ultrasonic scans having a plurality of times of ultrasonic transmission and reception as a basic unit, and acquires a plurality of reception signals respectively for a plurality of reception rasters allocated with respect to a predetermined region of a subject. The power information acquisition circuitry generates a plurality of first signals corresponding to the plurality of reception rasters respectively by performing adding processing or low-pass filtering having a time of the ultrasonic scan as a unit with respect to the plurality of reception signals respectively acquired for the plurality of reception rasters, and acquires power information of a moving body in the predetermined region based on a second signal to be obtained by performing an MTI filtering with respect to the plurality of first signals. The velocity information acquisition circuitry acquires velocity information of the moving body based on a third signal obtained by performing the MTI filtering with respect to the plurality of reception signals respectively acquired for the plurality of reception rasters. The image generating circuitry generates a Doppler image corresponding to the predetermined region based on the power information and the velocity information.

Hereinafter, a first embodiment to a third embodiment of the present invention will be described in accordance with the drawings. Incidentally, in the following description, components having substantially the same function and configuration will be attached with the same reference numerals and an overlapped description thereof will be made only in a necessary case.

(First Embodiment)

FIG. 1 is a block diagram illustrating a configuration of an ultrasonic diagnostic apparatus according to a first embodiment. As illustrated in FIG. 1, an ultrasonic diagnostic apparatus 1 is provided with an ultrasonic probe 12, an input interface circuit 13, a monitor 14, an ultrasonic transmitting circuit 20, an ultrasonic receiving circuit 21, an input buffer 22, a B-mode processing circuit 23, a color Doppler processing circuit 24, a FFT Doppler processing circuit 25, a RAW data memory 26, a volume data generating circuit 27, an image processing circuit 28, a display processing circuit 30, a control processor (CPU) 31, a storage circuit 32 and an interface circuit 33. Hereinafter, a description will be made regarding a function of individual component.

The ultrasonic probe 12 is a device (probe) that transmits an ultrasonic wave with respect to a subject having a living body as a typical example, and receives a reflected wave from the subject based on the transmitted ultrasonic wave, and has an array of a plurality of a plurality of piezoelectric vibrators (ultrasonic transducers), a matching layer, a backing material and the like at a distal end thereof. The piezoelectric vibrator transmits an ultrasonic wave to a desired direction in a scan region based on a driving signal from the ultrasonic transmitting circuit 20, and converts the reflected wave from the subject into an electrical signal. The matching layer is an intermediate layer that is provided in the piezoelectric vibrator and causes ultrasonic energy to be propagated with high efficiency. The backing material prevents propagation of the ultrasonic wave from the piezoelectric vibrator to a rear side. When the ultrasonic wave is transmitted from the ultrasonic probe 12 to the subject, the transmitted ultrasonic wave is sequentially reflected by a discontinuity surface of acoustic impedance of internal body tissue, and is received by the ultrasonic probe 12 as an echo signal. The amplitude of the echo signal depends on a difference in the acoustic impedance in the reflecting discontinuity surface. In addition, an echo in a case where a transmitted ultrasonic pulse is reflected by a moving blood flow depends on a velocity component of an ultrasonic transmitting and receiving direction of the moving body due to the Doppler effect, and is subjected to a frequency shift. In the present embodiment, the ultrasonic probe 12 is set to a one-dimensional array probe in which a plurality of the ultrasonic vibrators are arranged along a desired direction. However, the present invention is not bound to such an example, and the ultrasonic probe 12 may be configured to be capable of acquiring volume data, and to be a two-dimensional array probe (probe in which the plurality of ultrasonic vibrators are arranged in a two-dimensional matrix form) or a mechanical 4D probe (probe capable of performing the ultrasonic scan while mechanically swinging the ultrasonic vibrator array in a direction perpendicular to the array direction).

The input interface circuit 13 is connected to an apparatus body 11, and has various types of switches, buttons, a trackball, a mouse, a keyboard and the like which are used to input, to the apparatus body 11, various types of instructions, conditions, an instruction to set a region of interest (ROI), various types of image quality condition setting instructions, and the like from an operator such as selection of an imaging mode.

The monitor 14 is a display that displays morphological information in a living body and blood flow information acquired through a color Doppler mode as images based on video signals from the display processing circuit 30. In addition, the monitor 14 displays an ultrasonic image to be reproduced by a color Doppler imaging method, which will be described later, in a predetermined form together with a predetermined information.

The ultrasonic transmitting circuit 20 has a trigger generating circuit, a delay circuit, and a pulser circuit (which are not illustrated). The trigger generating circuit repetitively generates trigger pulses for the formation of transmission ultrasonic waves at a predetermined rate frequency fr Hz (period: 1/fr sec). In addition, in the delay circuit, a delay time necessary to focus an ultrasonic wave into a beam and determine transmission directivity for each channel is given to each trigger pulse. The pulser circuit applies a driving pulse to the probe 12 at the timing based on this trigger pulse. In addition, the ultrasonic transmitting circuit 20 performs ultrasonic transmission, which will be described later, based on a control signal from the control processor 31 in a color Doppler imaging process.

The ultrasonic receiving circuit 21 has an amplification circuit, an A/D converter, the delay circuit, an adder, a quadrature detection circuit, and the like (which are not illustrated). The amplification circuit amplifies the echo signal taken via the probe 12 for each channel. The A/D converter converts the amplified analog echo signal into a digital echo signal. The delay circuit determines reception directivity with respect to the echo signal converted into the digital signal, and gives the delay time necessary for performing reception dynamic focusing, and then the adder performs adding processing is performed. A reflection component from a direction corresponding to the reception directivity of the echo signal is enhanced through the adding processing, and a composite beam for ultrasonic transmission and reception is formed in accordance with the reception directivity and transmission directivity. The quadrature detection circuit converts an output signal of the adder into an in-phase signal (I signal) of a baseband, and a quadrature-phase signal (Q signal). The quadrature detection circuit outputs the I signal and the Q signal (IQ signal), as the echo signal, to a subsequent processing system. Incidentally, the quadrature detection circuit may perform conversion processing into a radio frequency (RF) signal. Incidentally, the ultrasonic receiving circuit 21 performs ultrasonic reception, which will be described later, based on a control signal from the control processor 31 in a color Doppler imaging process.

The input buffer 22 is a buffer that temporarily stores the echo signal (the IQ signal or the RF signal) output from the ultrasonic receiving circuit 21. The input buffer 22 is, for example, a first-in/first-out (FIFO) memory, and temporarily stores the IQ signals for several frames (or the IQ signals corresponding to several volumes). In addition, the input buffer 22 is a circuit that rewrites the IQ signal corresponding to the temporally oldest frame with the IQ signal, which has been newly received from the ultrasonic receiving circuit 21 in a case where the IQ signal for one frame is newly output from the ultrasonic receiving circuit 21.

The B-mode processing circuit 23 receives the echo signal from the receiving circuit 21, and performs logarithmic amplification, envelope detection processing, and the like for the signal to generate data of which signal intensity is expressed by a brightness level.

The color Doppler processing circuit 24 performs color Doppler processing using the echo signal (the IQ signal or the RF signal) received from the input buffer 22, and outputs a power signal and a velocity signal. Incidentally, the color Doppler processing circuit 24 has at least dual signal processing system including a first processing system that performs processing in relation to a power signal, and a second processing system that performs processing in relation to a velocity signal (see FIG. 2). A specific function of the color Doppler processing circuit 24 will be described later in detail.

The FFT Doppler processing circuit 25 performs fast Fourier transform using the acquired echo signal in a continuous wave Doppler mode, and outputs a spectrum signal.

The RAW data memory 26 generates B-mode RAW data, which is B-mode data on a three-dimensional ultrasonic scan line, using a plurality of the B-mode data received from the B-mode processing circuit 23. In addition, the RAW data memory 26 generates blood flow RAW data, which is blood flow data on the three-dimensional ultrasonic scan line, using a plurality of the blood flow data received from the color Doppler processing circuit 24. Incidentally, it may be configured such that a three-dimensional filter is inserted subsequently to the RAW data memory 26 to perform spatial smoothing for the purpose of reducing noise and improving image concatenation.

The volume data generating circuit 27 generates B-mode volume data and blood flow volume data by performing RAW-voxel conversion including an interpolation process in which spatial position information is added.

The image processing circuit 28 performs predetermined image processing such as volume rendering, multi planar reconstruction (MPR), and maximum intensity projection (MIP) for the volume data received from the volume data generating circuit 27. Incidentally, it may be configured such that a two-dimensional filter is inserted subsequently to the image processing circuit 28 to perform the spatial smoothing for the purpose of reducing the noise and improving the image concatenation.

The display processing circuit 30 performs various types of processes such as a dynamic range, brightness, contrast, γ curve correction, RGB conversion, and the like for various types of image data generated and processed by the image processing circuit 28.

The control processor 31 has a function as an information processing apparatus (computer), is a central processing unit (CPU) that controls each operation of components, and is configured by a processing circuitry and a memory. Further, the control processor 31 controls the ultrasonic transmitting circuit 20, the ultrasonic receiving circuit 21, the color Doppler processing circuit 24, and the like in a process (color Doppler imaging process) according to a color Doppler imaging function which will be described later.

The storage circuit 32 is used to store a program for implementing processing in relation to the ultrasonic transmission and reception and a Doppler signal, a diagnostic protocol, transmission and reception conditions and other data groups, which are implemented in the color Doppler imaging process which will be described later. In addition, the storage circuit 32 is also used to store images in an image memory (not illustrated) if necessary. It is possible to transfer data in the storage circuit 32 to an external peripheral apparatus via the interface circuit 33.

The interface circuit 33 is an interface for connection with a new outer storage apparatus (not illustrated) such as the input interface circuit 13 and a network interface circuit. It is also possible to connect another apparatus to the ultrasonic diagnostic apparatus body 11 via the interface circuit 33. In addition, it is possible to transfer data such as the ultrasonic image, analysis results, obtained by the apparatus, to another apparatus via the network by the interface circuit 33.

(Configuration of Color Doppler Processing Circuit 24)

FIG. 2 is a diagram illustrating a block configuration of the color Doppler processing circuit 24. The color Doppler processing circuit 24 is configured by the processing circuitry and the memory. Further, the color Doppler processing circuit 24 implements the two system of the first processing system (a power processing system P) and the second processing system (a velocity processing system V) by causing a dedicated program stored in the memory to be executed by the processing circuitry.

The first processing system is configured by an intra-frame data adding function 241, a first calculation function 243, a first MTI filter function 245, a power estimation function 247, and a LOG compression processing function 249. Further, the second processing system is configured by a second calculation function 242, a second MTI filter function 244, and a velocity estimation function 246.

In the first processing system, the intra-frame data adding function 241 adds the echo signals at the same reception positions in the same frame using the echo signal (the IQ signal or the RF signal) for each frame output from the input buffer 22. The first calculation function 243 sequentially calculates correlation matrices between frames using the echo signal (the added echo signal) obtained by adding a plurality of signals at the same reception positions in the frame as a signal. Further, the first calculation function 243 sequentially calculates coefficients of the MTI filter based on the obtained correlation matrix. The first MTI filter 245 applies the MTI filter between the frames while adaptively changing the coefficient using the coefficients sequentially calculated by the first calculation function 243. The power estimation function 247 estimates the power signal using a component extracted in the first MTI filter 245. The LOG compression processing function 249 performs LOG compression of the estimated power signal and output the resultant to the subsequent processing system.

Further, in the second processing system, the second calculation function 242 sequentially calculates intra-frame and inter-frame correlation matrices using the echo signals (a data string having an unequal time interval) at the same reception positions over a plurality of the frames. Further, the second calculation function 242 sequentially calculates coefficients of the MTI filter based on the obtained correlation matrix. The second MTI filter function 244 applies the MTI filter between the frames while adaptively changing the coefficient using the coefficients sequentially calculated by the second calculation function 242. The velocity estimation function 246 estimates the blood flow velocity using a component extracted in the second MTI filter function 244.

(Color Doppler Imaging Process)

FIG. 3 is a flowchart illustrating a flow of the color Doppler imaging process to be implemented by the ultrasonic diagnostic apparatus 1 according to the present embodiment. Hereinafter, a description will be made in detail regarding a process performed in each step.

[Ultrasonic Transmission and Reception: Step S1]

Figure 4:
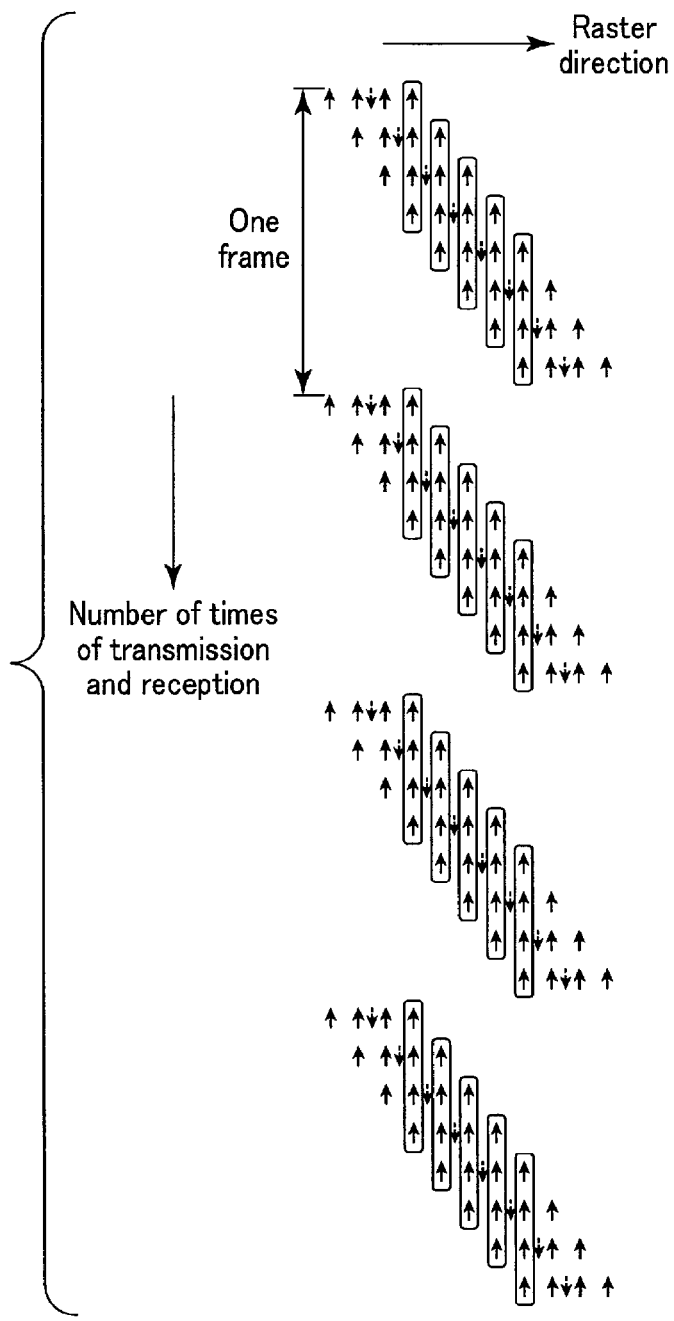
FIG. 4 is a diagram illustrating an example of ultrasonic transmission and reception to be performed in the Doppler imaging of the ultrasonic diagnostic apparatus according to the embodiment.

FIG. 4 is a diagram illustrating an example of the ultrasonic transmission and reception to be performed in the Doppler imaging of the ultrasonic diagnostic apparatus 1. In FIG. 4, the downward arrow indicates one-time ultrasonic transmission, a position on the horizontal axis of the downward arrow on indicates an ultrasonic transmission position in relation to a raster direction (that is, transmitting direction), and a position on the vertical axis of the downward arrow indicates the number of times of transmission. Further, the upward arrow indicates one-time ultrasonic reception, a position on the horizontal axis of the upward arrow on indicates an ultrasonic reception position in relation to the raster direction (that is, receiving direction), and a position on the vertical axis of the upward arrow indicates the number of times of reception.

As illustrated in FIG. 4, the ultrasonic transmission and reception in the color Doppler imaging process repeatedly performs, as a basic unit, parallel simultaneous reception in which reception signals of a plurality of directions (the plurality of reception rasters) can be obtained at one-time transmission. Incidentally, FIG. 4 illustrates an example at the time of four-direction parallel simultaneous reception for one-time transmission in order to specify the description. However, the number of parallel simultaneous reception corresponding to one-time transmission (that is, the basic unit) may be any number.

Further, the control processor 31 performs a scan of one frame while shifting the transmission position by a reception raster for each transmission in each frame. In this manner, as illustrated in FIG. 4, eight times of transmission are performed in a frame, and four signals (four echo signals corresponding to the reception raster in the same picture frame) having the same reception position although having different transmission positions are successively acquired position for the plurality of frames.

[First Processing (Power Signal Processing): Step S2A]

FIG. 5A is a diagram for describing processing in relation to the power signal to be performed in the first processing system (WF1) of the color Doppler processing circuit 24. FIG. 6A is a diagram in which the "number of times of transmission and reception" in the vertical direction of FIG. 5A is drawn in the horizontal direction regarding the echo signal from a certain depth on a predetermined reception raster. Incidentally, data strings described by "a1, a2, a3 and a4", "b1, b2, b3 and b4", "c1, c2, c3 and c4" and so on in WF2 of FIG. 6A are data strings of the echo signal at the same reception position received by the second processing system.

As illustrated in FIG. 6A, the intra-frame data adding function 241 adds the four echo signals at the same reception position although having different transmission positions in one frame (four IQ signals or RF signals in the red frame of FIG. 5A, that is, "a1, a2, a3 and a4" and the like of FIG. 6A), and generates added echo signals A, B, C, D and so on for each raster in each frame. The added echo signal to be obtained by the addition can be expressed by, for example, the following Equation 1.

$$A = a_1 + a_2 + a_3 + a_4$$
$$B = b_1 + b_2 + b_3 + b_4 \quad (1)$$

In general, when a signal including random noise is added N times, an S/N is improved by a square root of N. Accordingly, when the signal is added four times as in the present embodiment, an S/N is improved twice, that is, by 6 dB. Incidentally, in a case where an amplitude signal or the power signal is added, an S/N is not improved. Thus, it is necessary to perform addition at a point in time of the IQ signal or the RF signal in a coherent state in order to improve the S/N.

Next, the first calculation function 243 calculates the correlation matrices between frames using the obtained data strings A, B, C, D and so on of the added echo signal. Incidentally, although it is possible to set the number L of the data strings to be used in the corresponding inter-frame correlation matrix in an arbitrary manner, here, a case will be exemplified in which L=4, and four data are used in order to specify the description. Specifically, as the data string, a data string is used by shifting one by one as the frame number increases, for example, data of A, B, C and D in an output frame 1, data of B, C, D and E in an output frame 2, and data of C, D, E and F in an output frame 3.

The data string used in Output Frame 1 can be formulated as the following Equation 2.

$$x_m = \begin{pmatrix} A_m \\ B_m \\ C_m \\ D_m \end{pmatrix} \quad (2)$$

As described above, the data string of A, B, C and D is a row of the echo signals from a certain depth on a certain reception raster. Further, in case where a subscript m is attached, it is considered that a particular position, that is, a two-dimensional or three-dimensional m-th position is indicated, and that it is possible to acquire information from M spatial positions as a whole.

A correlation matrix Rxx according to a spatial ensemble average can be formulated as the following Equation 3.

$$R_{xx} = \sum_{m=1}^{M} x_m x_m^H \quad (3)$$

Here, a subscript H represents a complex conjugate transpose (Hermitian transpose). It may be configured such that a correlation matrix is calculated using data of the entire range of a color Doppler scan, or that the scan range is divided into blocks, and then, each correlation matrix is calculated for each block, as M ranges. The above-described correlation matrix Rxx is a matrix of L×L. Incidentally, a covariance matrix may be used instead of the correlation matrix. Here, the covariance matrix is obtained by performing an arithmetic operation of the above-described Equation 3 with respect to a signal xm obtained by subtracting an average value in advance.

Next, the first calculation function 243 calculates an eigenvalue and an eigenvector for the obtained correlation matrix Rxx of L×L. When a matrix in which the eigenvalues are arranged from the left in a descending order with the eigenvector as a column vector is set to V, and the echo signal is approximated with K principal components from the top, it is possible to express the correlation matrix Rxx as the following Equation 4.

$$V \begin{pmatrix} 1 & & & & \\ & 1 & & & \\ & & \ddots & & \\ & & & 0 & \\ & & & & 0 \end{pmatrix} V^H x \quad (4)$$

Here, the center matrix is a diagonal matrix, and in diagonal elements, the number of "1" is K from the upper left and the remaining components are "0".

Next, the first calculation function 243 subtracts the component represented by the above-described Equation 4 from an original signal x. Since V is a unitary matrix, a result of the subtraction can be expressed by the following Equation 5.

$$x - V \begin{pmatrix} 1 & & & & \\ & 1 & & & \\ & & \ddots & & \\ & & & 0 & \\ & & & & 0 \end{pmatrix} V^H x = V \begin{pmatrix} 0 & & & & \\ & 0 & & & \\ & & \ddots & & \\ & & & 1 & \\ & & & & 1 \end{pmatrix} V^H x \quad (5)$$

The first calculation function 243 calculates a coefficient by multiplying a matrix W expressed by the following Equation 6 to an input data string x, and determines a configuration of the MTI filter.

$$W = V \begin{pmatrix} 0 & & & & \\ & 0 & & & \\ & & \ddots & & \\ & & & 1 & \\ & & & & 1 \end{pmatrix} V^H \quad (6)$$

Incidentally, in the above-described Equation 6, K becomes the number of "0" in the center diagonal matrix. This becomes a process of reducing a rank of the matrix, and accordingly, K will be referred to as a rank-cut number.

The first MTI filter function 245 performs the MTI filtering, defined by the matrix W, to the input data string x, and outputs a data string y represented by the following Equation 7.

$$y = W_x \quad (7)$$

The power estimation function 247 performs calculation represented by the following Equation 8 with respect to the data string y from the first MTI filter function 245, and acquires a power value P0.

$$P_0 = y^H y \quad (8)$$

The LOG compression processing function 249 performs the log compression according to the following Equation 9, and acquires a power value P to be used at the end.

$$P = \log(P_0) \quad (9)$$

In the ultrasonic transmission and reception illustrated in FIG. 5A, when an ultrasonic transmission interval is set as T, 8T becomes 1 frame time. Accordingly, an interval of the data string of A, B, C and D of the first processing system is given "1 frame time=8T", and the aliasing velocity is given as the following Equation 10.

$$V'_{max} = \frac{C}{4f_0(8T)} \quad (10)$$

[Second Processing (Velocity Signal Processing): Step S2B]

Figure 5B:
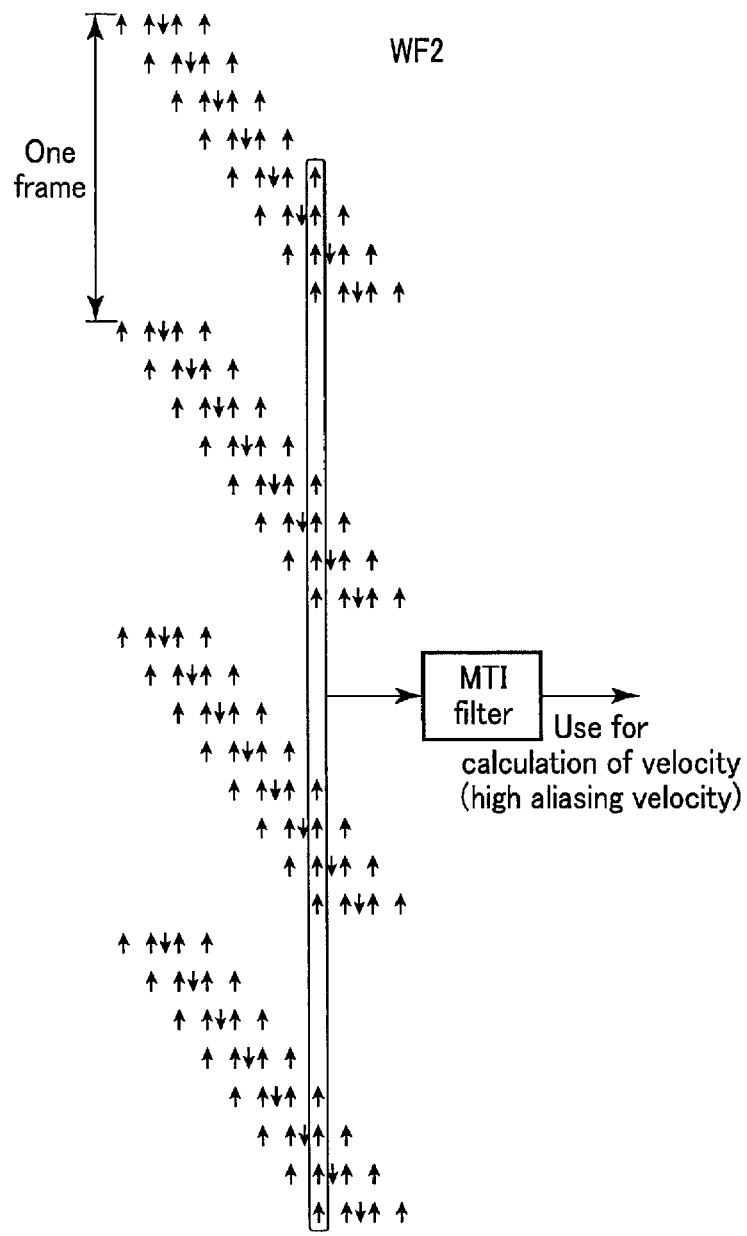
Figure 6A:
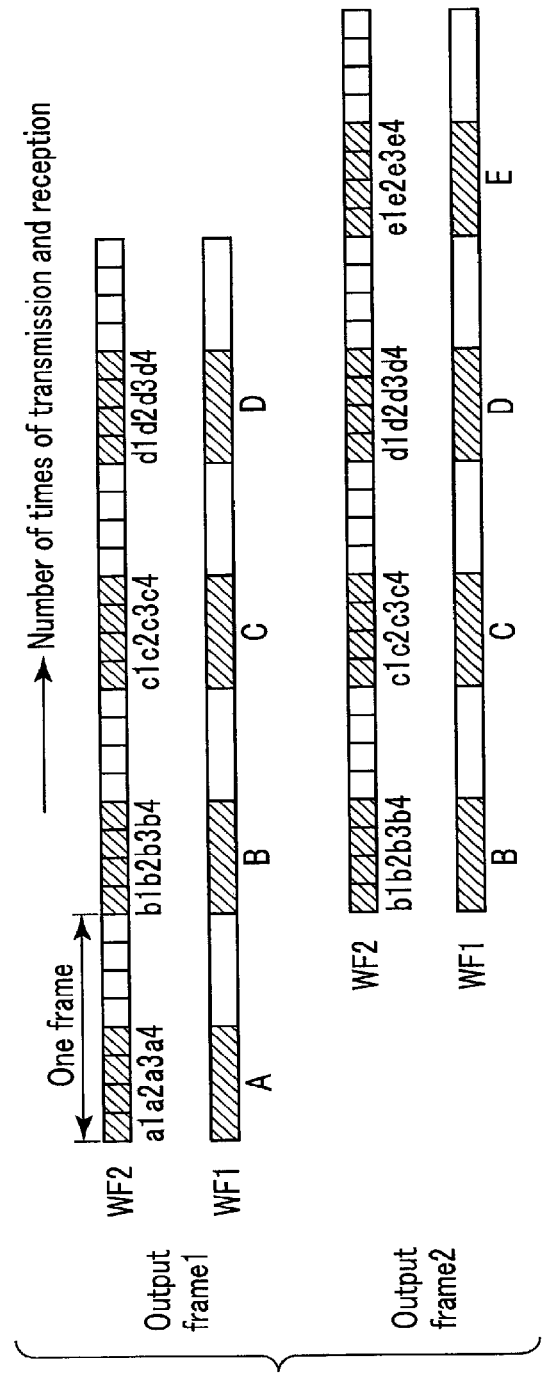
FIGS. 6A and 6B are diagrams for describing the signal processing to be performed in the first processing system and the second processing system of the color Doppler processing circuit 24.

FIG. 5B is a diagram for describing processing in relation to the velocity signal to be performed in the second processing system (WF2) of the color Doppler processing circuit 24.

Next, the second calculation function 242 calculates the intra-frame and inter-frame correlation matrices using a plurality of the echo signals having the same reception position although having different transmission positions as an input data string over the plurality of frames. Incidentally, although it is possible to set a length L of the data string to be used in the corresponding inter-frame and inter-frame correlation matrix calculation in an arbitrary manner, here, data present in the same observation time as the first processing is used in order to specify the description. Accordingly, as illustrated in FIG. 6A, the data string present in the same observation time as WF1 in Output Frame 1 can be expressed by the following Equation 11 as a vector having 16 elements of "a1, a2, a3 and a4" to "d1, d2, d3 and d4" described as WF2 (corresponding to 16 IQ signals or RF signals in the red frame of FIG. 5B).

$$x = \begin{pmatrix} a_1 \\ a_2 \\ \vdots \\ d_4 \end{pmatrix} \quad (11)$$

In other words, the same processing as the first processing (WF1) is performed with L=16. Accordingly, the correlation matrix Rxx is given as a matrix of 16×16. It should be noted that the processing has been performed with respect to an equally spaced data string in the first processing but the processing is performed with respect to an unequally spaced data string in the second processing. A method of removing clutter from an ultrasonic signal of the equally spaced data string by principal component analysis is disclosed in Bjaerum, Torp, Kristoffersen, "Clutter filters adapted to tissue motion in ultrasound color flow imaging", IEEE Trans. Ultrason., Ferroelect., Freq. Contr., vol. 49, pp. 693-704, June 2002. However, a method of using the principal component analysis as a method of removing clutter from an ultrasonic signal of the unequally spaced data string is a feature of the color Doppler imaging function according to the present embodiment.

The second calculation function 242 performs the principal component analysis with respect to the unequally spaced data string, and gives a rank-cut number K, different from that of the first processing, and determines the MTI filter matrix W. The second MTI filter function 244 performs the MTI filtering using the determined MTI filter matrix W, and generates an output data string illustrated in FIG. 6B.

Figure 6B:
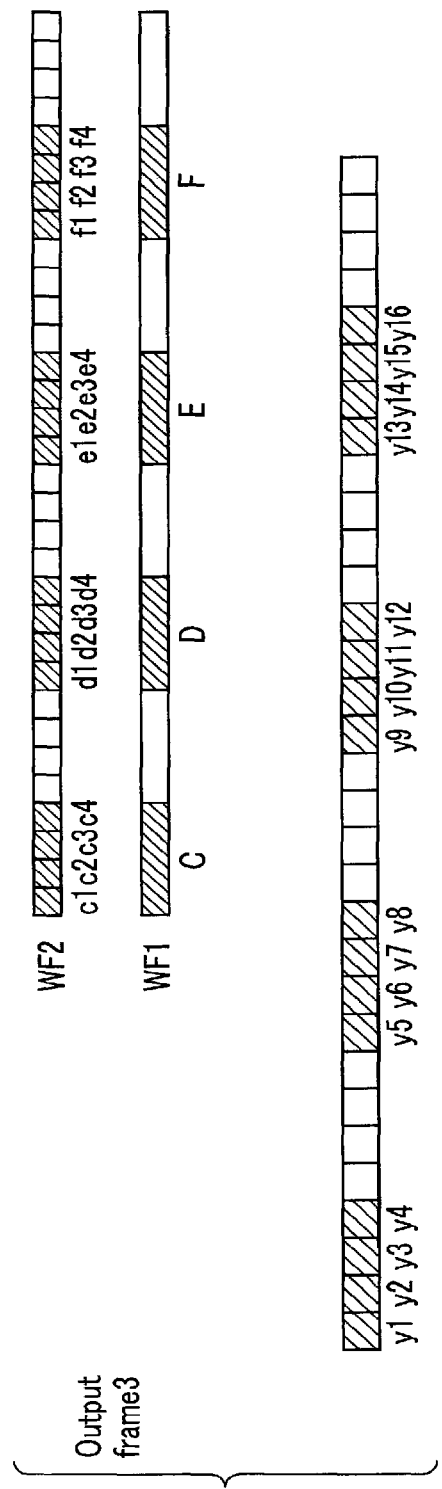

The velocity estimation function 246 calculates the blood flow velocity using a data string in which the entire data of a pulse pair performing autocorrelation calculation is surrounded by data having a short period in order to avoid influence from an end portion of the generated data string. For example, in a case where the output data string illustrated in FIG. 6B is used, the velocity estimation function 246 calculates an autocorrelation function c1 according to the following Equation 12.

$$c_1 = y_2^* y_3 + y_6^* y_7 + y_{10}^* y_{11} + y_2^* y_3 + y_{14}^* y_{15} \quad (12)$$

Here, "*" indicates a complex conjugate. Incidentally, in a case where all the pulse pairs having the short period are used, the S/N is also favorable. Thus, the velocity estimation function 246 may be configured to calculate the autocorrelation function c1 by the following Equation 13.

$$c_1 = \sum_{i=1}^{15} y_i^* y_{i+1} \quad (13)$$

The velocity estimation function 246 calculates the blood flow velocity by the following Equation 14 using the obtained autocorrelation function c1 as described above.

$$V = a\tan 2(\text{imag}(c_1), \text{real}(c_1)) \quad (14)$$

Here, a tan 2 is an arctangent function that calculates an angle in a range of $-\pi$ to $\pi$. At this time, the aliasing velocity can be obtained by the following Equation 15.

$$V_{max} = \frac{C}{4 f_0 T} \quad (15)$$

When comparing Equation 10 and Equation 15, it is understood that the aliasing velocity of the second processing is eight times the aliasing velocity of the first processing. That is, it is possible to implement a high aliasing velocity according to the second processing according to the present embodiment.

[Process of Generation and Display of Doppler Image: Steps S3 and S4]

The image processing circuit 28 generates the Doppler image using the power value P obtained by the first processing system and a velocity value V obtained by the second processing system. The generated Doppler image is subjected to predetermined processing in the display processing circuit 30, and then, is displayed on the monitor 14 in a predetermined form, for example, in a velocity display mode in which the velocity value V is displayed only in a case where the power value P is equal to or larger than a certain threshold value, in a power with direction display mode in which color coding is performed into red and blue depending on reference signs of the velocity value V, and brightness is changed depending on the power value P, and the like. According to such a display, it is possible to display a minute blood flow in the state with little noise in the velocity display mode, and thus, it is possible to display the velocity value with the high aliasing velocity. In the power with direction display mode, it is possible to perform the display without error in the color coding of directions even at high flow rate, and it is also possible to simultaneously display the minute blood flow at high flow rate.

(Modified Example 1)

In Step S1 of the embodiment described above, the parallel simultaneous transmission and reception is performed by shifting the transmission position by a reception raster for each transmission and the power signal and the velocity signal are calculated, respectively, in the first processing system and the second processing system using the obtained echo signal string as illustrated in FIGS. 4 to 5B.

Figure 7:
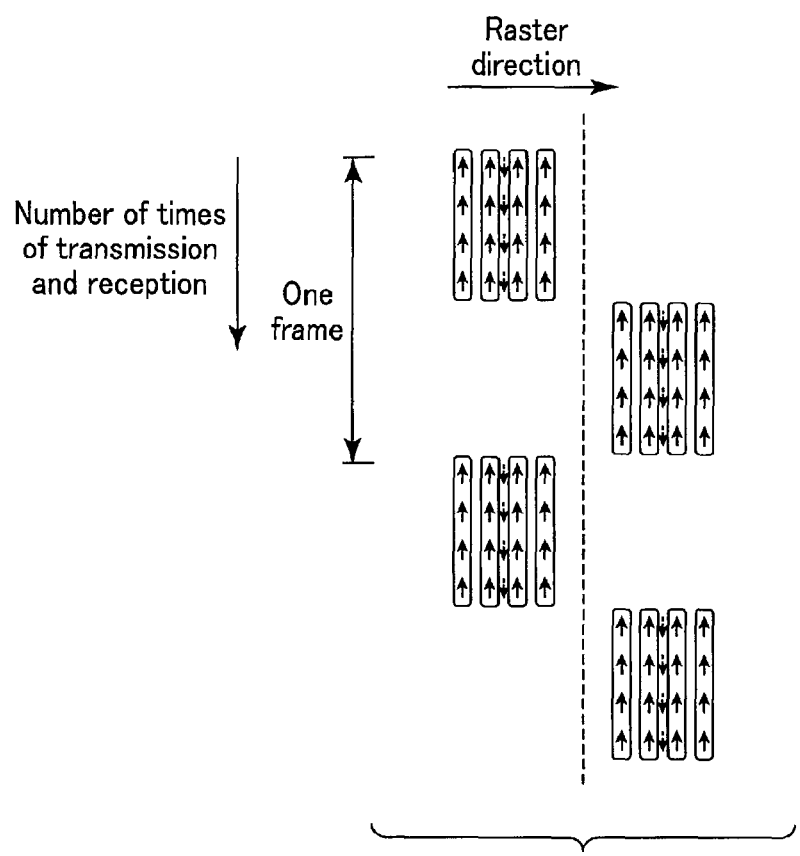
FIG. 7 is a diagram illustrating another example of ultrasonic transmission and reception performed in the ultrasonic diagnostic apparatus according to the embodiment.

However, the present invention is not limited to such an example, and may be configured such that the parallel simultaneous transmission and reception is performed without shifting the transmission position for each transmission and the power signal and the velocity signal are calculated, respectively, in the first processing system and the second processing system using the obtained echo signal as illustrated in FIG. 7. Incidentally, in the example of FIG. 7, it is exemplified that the parallel simultaneous transmission and reception is performed for each frame while shifting the transmission position, with a plurality of times (four) of transmission as the basic unit, by the plurality of reception rasters (four to five rasters).

Incidentally, in ultrasonic transmission and reception according to Modified Example 1, there is a need for a process of collectively shifting the transmission position in unit of block (corresponding to the dotted line in FIG. 7). Accordingly, there is no need for such collective shifting in the ultrasonic transmission and reception illustrated in FIGS. 4 to 5B, and accordingly, there is an effect of not generating difference in level between blocks due to discontinuity at a point at which the transmission position is changed.

(Modified Example 2)

In Step S2 of the embodiment described above, the coefficient of the MTI filter is adaptively determined using the principal component analysis (or a process mathematically equivalent thereto) that uses the correlation matrix or the covariance matrix with respect to the unequally spaced data string. However, the present invention is not bound to such an example, and it may be configured such that the coefficient of the MTI filter is adaptively determined with respect to the unequally spaced data string by approximating the clutter using polynomial fitting, for example, and subtracting the clutter from the original signal (or by performing a process mathematically equivalent thereto).

(Comparative Example)

FIGS. 8A to 8E are diagrams for describing an effect of the ultrasonic diagnostic apparatus according to the present embodiment, and illustrate images in which the power with the direction of the blood flow is displayed. In each drawing, in a case where there is no aliasing, a red (dot) region represents the blood flow flowing toward the ultrasonic probe 12, a blue (oblique line) region represents the blood flow flowing out, and brightness represents the magnitude of power. A gray scale (no pattern) region is a region in which the power value is equal to or smaller than the threshold value and a B-mode image is visible. Incidentally, the number of reception of the same raster in the frame is five.

Figure 8E:
FIGS. 8A to 8E are diagrams for describing a Doppler image to be generated and displayed by the ultrasonic diagnostic apparatus according to the embodiment.
Figure 8D:
Figure 8C:
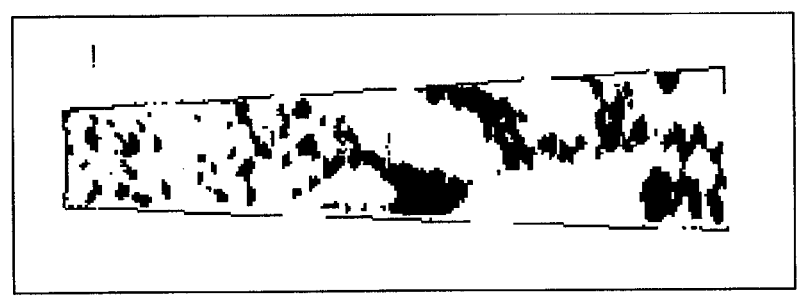
Figure 8B:
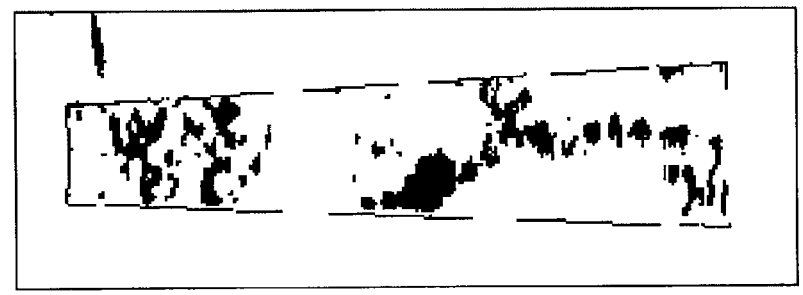
Figure 8A:
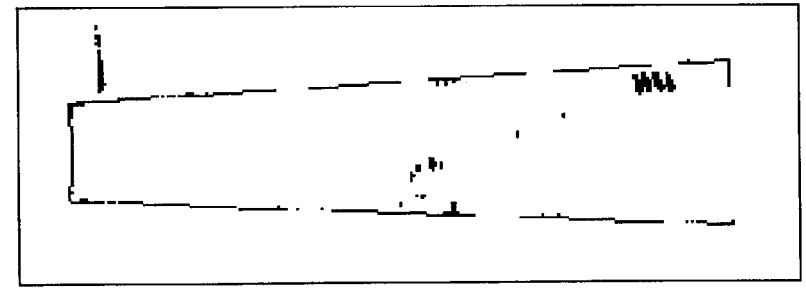

FIG. 8A is the diagram in which the power and the velocity are obtained by applying the MTI filter only with respect to five data in a frame, and displayed. As understood from FIG. 8A, the observation time is short so that the low flow rate is almost undetectable.

FIG. 8B is the diagram in which the power and the velocity are obtained by applying the MTI filter with respect to data of 16 frames using one data without performing the adding processing in a frame, and then displayed. It is understood that a kidney blood flow is expressed, but red (dot) and blue (oblique line) are mingled, and multiple aliasing phenomena are generated.

FIG. 8C is the diagram in which only the first processing is performed using data of 16 frames with the added echo signal obtained by adding five data in a frame as a signal, and the power and the velocity of the first processing are used to be displayed. As compared to FIG. 8B, it is understood that brightness of a part having no blood flow is dark, the S/N is improved, and more minute blood flow is also observed in FIG. 8C.

FIG. 8D is the diagram in which only the second processing is performed and the power and the velocity of the second processing are used to be displayed. As compared to FIGS. 8B and 8C, it is understood that the aliasing is greatly reduced in FIG. 8D, an artery of the kidney is displayed in red, and a vein thereof is displayed in blue so that two blood vessels are separately visible due to each color.

FIG. 8E is the diagram in which the power (power in FIG. 8C) of the first processing and the velocity (velocity in FIG. 8D) of the second processing are used to generate and display the Doppler image. Although noise is visible around the minute blood flow in the example of FIG. 8D, the brightness of the minute blood flow is increased so that the minute blood flow is more clearly observed in the example of FIG. 8E.

According to the ultrasonic diagnostic apparatus according to the present embodiment, the echo signals (the IQ signal or the RF signal) having the same reception position in the same frame are added in the first processing system, the obtained added echo signal is set as a signal, and the MTI filter is applied between frames. The MTI filter is performed by a method of approximating the clutter with the principal component analysis and subtracting the clutter from the original signal. The filter coefficients of the MTI filter are sequentially updated based on the obtained echo signals, and thus, can adaptively react to a motion, and prevent generation of the motion artifact. Further, since the filter coefficient of the MTI filter is determined using the added echo signal, it is possible to improve the S/N as compared to the related art. Here, in the first processing system, a problem is not generated in which the image appears to be discontinuous when the transmission position is different since the difference in the transmission positions is completely canceled so as to add the signal having the same reception position although having the different transmission position. In addition, since the interval of data to be used for calculation of the filter coefficient of the MTI filter is one frame, it is possible to implement an excellent sensitivity to the low flow rate. Incidentally, although the aliasing velocity in the first processing system is set to the low state, an object to be calculated in the first processing system is the power information. Accordingly, there is no problem even when there occurs the aliasing velocity in the first processing system.

Further, according to the ultrasonic diagnostic apparatus according to the present embodiment, the principal component analysis is performed using the echo signal (the IQ signal or the RF signal) having the same reception position is used as the unequally spaced data string without addition for several frames in the second processing system. It is possible to implement the MTI filter that is adaptively changed even with respect to the unequally spaced data string by subtracting the original signal from the principal component obtained above. The velocity is estimated using the pulse pair having the short data interval in the MTI filter output signals. Further, the aliasing velocity increases as being determined depending on a reception interval T, and the aliasing is hardly generated. Incidentally, a gap caused by different transmission is generated between the reception rasters since the signal having the same reception position although having different transmission positions are directly used in the second processing system. However, such a phase change is periodic and can be detected as the principal component in the principal component analysis so that it is possible to suppress influence thereof, and thus, a significant error is not generated in the velocity information to be obtained in the second processing.

(Second Embodiment)

The first embodiment exemplifies a case in which only the color Doppler scan is performed in Step S1 of FIG. 3. On the contrary, in a second embodiment, a description will be made regarding a case in which a B-mode scan is also performed together with the color Doppler scan.

Figure 9:
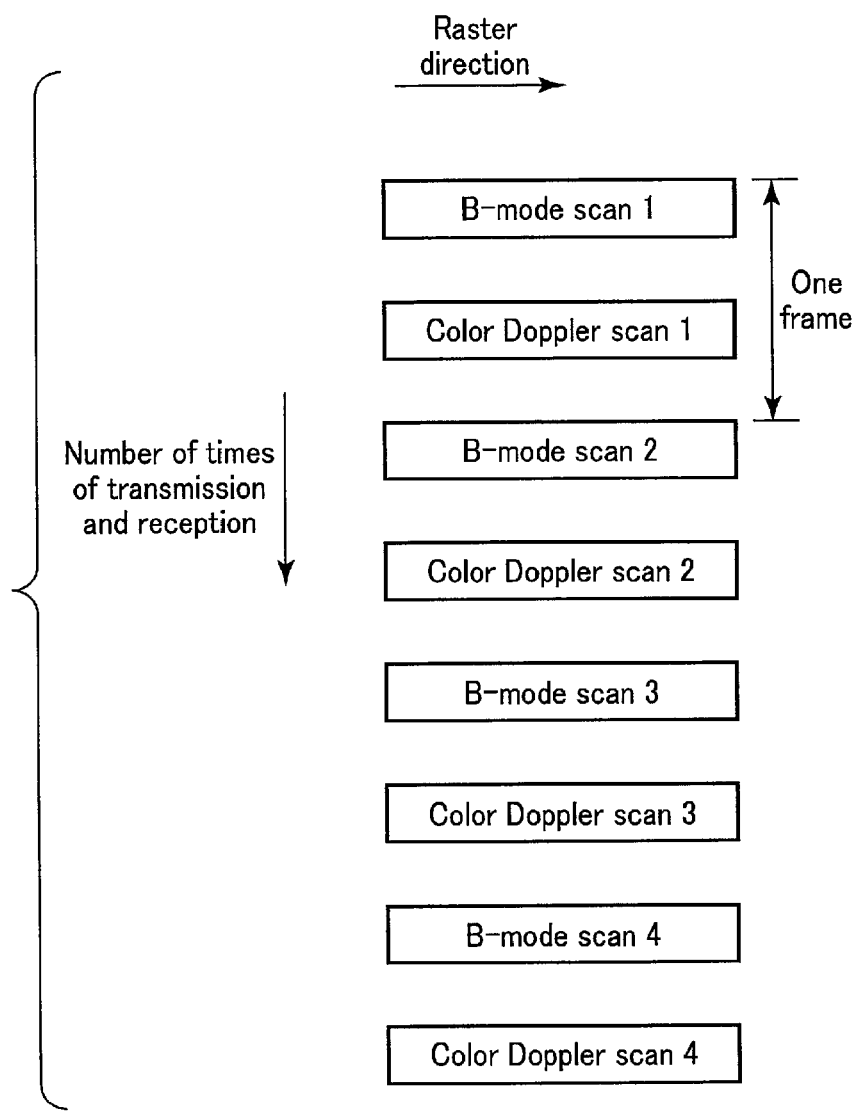
FIG. 9 is a flowchart illustrating a scan sequence to be implemented in Doppler imaging of an ultrasonic diagnostic apparatus according to a second embodiment.

FIG. 9 is a diagram for describing the ultrasonic transmission and reception to be performed in Step S1 of FIG. 2 by an ultrasonic diagnostic apparatus according to the second embodiment. As illustrated in FIG. 9, the B-mode scan for 1 frame is performed in the "B-mode scan", and the color Doppler scan for 1 frame is performed in the "color Doppler scan". Here, the "color Doppler scan" means the scan (that is, the scan by performing the parallel simultaneous transmission and reception in which the transmission position is shifted for a reception raster for each transmission) illustrated in FIG. 4 or the scan according to Modified Example 1.

The ultrasonic diagnostic apparatus according to the second embodiment is different from the ultrasonic diagnostic apparatus according to the first embodiment in that the aliasing velocity in the first processing is reduced since the frame time increases by time for the B-mode scan. However, there is no change in the aliasing velocity in the second processing. Here, since relatively long time required in the unequally spaced data string further increases, a property of the MTI filter according to the principal component analysis deteriorates, and there is a possibility that the clutter is not allowed to be sufficiently removed in the second processing.

(Third Embodiment)

Figure 10:
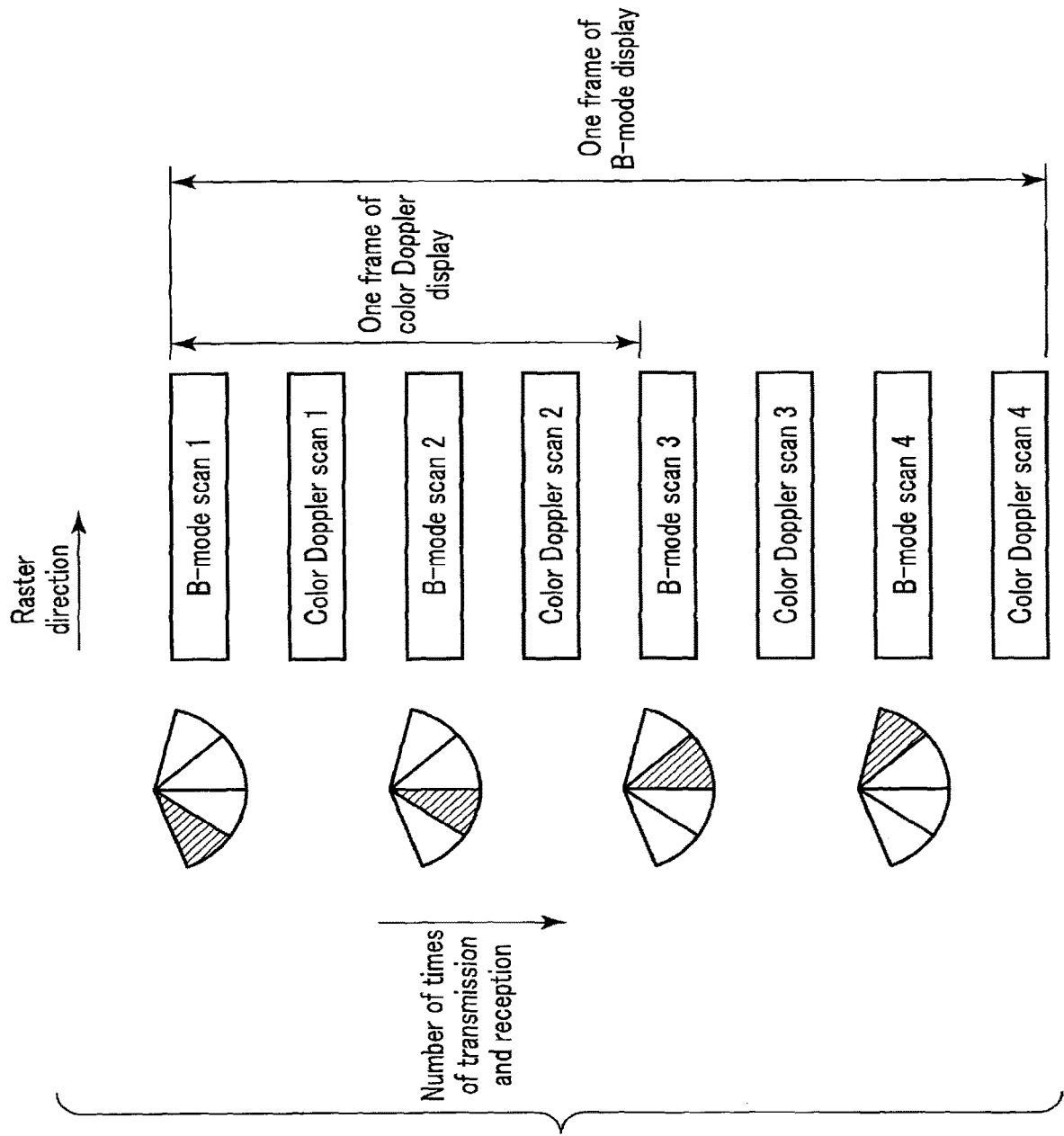
FIG. 10 is a flowchart illustrating the scan sequence to be implemented in the Doppler imaging of the ultrasonic diagnostic apparatus according to the second embodiment.

FIG. 10 is a diagram for describing the ultrasonic transmission and reception to be performed in Step S1 of FIG. 3 by an ultrasonic diagnostic apparatus according to a third embodiment. As illustrated in FIG. 10, the ultrasonic diagnostic apparatus according to the present embodiment performs the B-mode scan for every part (for every ¼ of the entire region in the example of FIG. 10) in the entire region to be scanned by ultrasonic wave in a case where the color Doppler scan and the B-mode scan are performed.

That is, a first ¼ is scanned in "B-mode scan 1", and then a next ¼ is scanned in "B-mode scan 2". Accordingly, the entire scan is completed at four times. On the other hand, in the color Doppler scan, the entire region is scanned in each scan as similarly to the first embodiment or Modified Example 1 thereof. Accordingly, it is possible to generate and display the Doppler image for each period of the "color Doppler scan". Here, a case is assumed in which a period of the color Doppler scan exceeds 60 fps, and the color Doppler image of a frame is displayed in two periods of the color Doppler scan. For example, in a case where the period of the color Doppler scan is 120 fps, the color Doppler is displayed at 60 fps, and the B-mode is displayed at 30 fps.

According to the ultrasonic diagnostic apparatus according to the present embodiment, it is possible to prevent the period of the color Doppler scan from increasing due to the B-mode scan.

Incidentally, the present invention is not limited to the above-described embodiments, and components can be modified and embodied in the execution stage within a scope of not departing from a gist of the invention. Specific modified examples are as follows, for example.

It is possible to implement each function according to the embodiments by installing a program that executes the corresponding processing to a computer such as a workstation, and causing the program to be deployed on a memory.

At this time, it is possible to store the program, which can cause the computer to execute the corresponding technique, in a recording medium such as a magnetic disk (a floppy (registered trademark), a hard disk and the like), an optical disk (CD-ROM, DVD and the like) and a semiconductor memory.

It is also possible to implement, in an ex-post manner, the generation and display of the Doppler image using the processing by the first processing system and the second processing system according to the above-described embodiment, using the IQ signal or the RF signal acquired in advance in the color Doppler mode in the ultrasonic image processing apparatus In the first processing system according to the above-described embodiments, the four echo signals having the same reception position although having the different transmission positions in a frame are added to generate the added echo signal for each raster in each frame. The low-pass filtering may be performed as the processing equivalent thereto.

It has been exemplified a case in which the first processing system and the second processing system according to the above-described embodiments are implemented by causing the processing circuitry to execute the dedicated program stored in the memory in the color Doppler processing circuit 24. However, the present invention is not limited thereto and each of the first processing system and the second processing system may be implemented using a hardware configuration such as a processing circuitry and the memory.

Incidentally, the above described "processing circuitry" means, for example, a central processing unit (CPU), a graphics processing unit (GPU), an application specific integrated circuit (ASIC), a programmable logical device (e.g., a simple programmable logic device (SPLD), a complex programmable logic device (CPLD), and a field programmable gate array (FPGA)), or the like.

Note that programs may be directly incorporated in processing circuitry instead that programs are stored in a memory 5m. In this case, the processing circuitry reads programs incorporated in circuitry and executes the programs to realize predetermined functions.

Each function (each component) in the present embodiment is not necessary to be corresponded to a single processing circuit and may be realized by a plurality of processing circuits. To the contrary, for example, at least two functions (at least two components) may be realized by a single processing circuit. Further, a plurality of functions (a plurality of components) may be realized by a single processing circuit.

In addition, it is possible to form various types of inventions by suitably combining a plurality of the components disclosed in the above-described embodiment. For example, some components may be removed from the entire component illustrated in the embodiment. Further, components may be suitably combined over different embodiments.

The invention claimed is:

1. An ultrasonic diagnostic apparatus comprising:
processing circuitry configured to:
cause a probe to perform ultrasonic transmission while changing a direction of the ultrasonic transmission over multiple transmission directions,
acquire, in response to the ultrasonic transmission in each of the multiple transmission directions, a plurality of reception signals for a plurality of reception rasters, respectively, wherein the reception rasters are allocated to a predetermined region of a subject,
acquire power information of a moving object in the predetermined region by
calculating a first signal for each of the reception rasters, wherein the first signal is calculated by adding together the reception signals that have been acquired for a respective one of the reception rasters in response to the ultrasonic transmission in the multiple transmission directions for a predetermined period,
calculating a second signal for each of the reception rasters, wherein the second signal is calculated by subjecting the first signal for the respective one of the reception rasters to first moving target indicator (MTI) filtering, and
calculating the power information based on the second signal,
acquire velocity information of the moving object by
calculating a third signal for each of the reception rasters, wherein the third signal is calculated by subjecting, to second MTI filtering, the reception signals that have been acquired for a respective one of the reception rasters in response to the ultrasonic transmission in the multiple transmission directions for the predetermined period and for a plurality of past periods consecutively preceding the predetermined period, and
calculating the velocity information based on the third signal, and
generate a Doppler image corresponding to the predetermined region based on the power information and the velocity information.

2. The ultrasonic diagnostic apparatus according to claim 1, wherein
the predetermined period and the past periods each correspond to one frame, the multiple transmission directions differ from each other by one reception raster width, and the processing circuitry is configured to cause the probe to shift a transmission position by a distance of the one reception raster width upon performing the ultrasonic transmission in each of the multiple transmission directions during the predetermined period and the past periods.

3. The ultrasonic diagnostic apparatus according to claim 2, wherein
the processing circuitry is configured to cause the probe to shift transmission positions.

4. The ultrasonic diagnostic apparatus according to claim 1, wherein the second MTI filtering comprises
approximating clutter with an eigenvalue and an eigenvector of a correlation matrix or a covariance matrix of the reception signals that have been acquired for the respective one of the reception rasters for the predetermined period and the past periods, and
subtracting the clutter from the reception signals that have been acquired for the respective one of the reception rasters for the predetermined period and the past periods.

5. The ultrasonic diagnostic apparatus according to claim 1, wherein the second MTI filtering comprises
approximating clutter with polynomial fitting of the reception signals that have been acquired for the respective one of the reception rasters for the predetermined period and the past periods, and
subtracting the clutter from the reception signals that have been acquired for the respective one of the reception rasters for the predetermined period and the past periods.

6. The ultrasonic diagnostic apparatus according to claim 1, wherein
the processing circuitry is configured to estimate velocity of the moving object in the predetermined region using an interval between a pulse pair having a predetermined data interval among the third signal.

7. The ultrasonic diagnostic apparatus according to claim 1, wherein the first MTI filtering comprises
approximating clutter with an eigenvalue and an eigenvector of a correlation matrix or a covariance matrix of the first signal calculated for the predetermined period and first signals calculated for the past periods for a corresponding, respective one of the reception rasters, and
subtracting the clutter from the first signal calculated for the predetermined period.

8. The ultrasonic diagnostic apparatus according to claim 1, wherein
the processing circuitry is configured to alternately perform a B-mode scan in relation to the predetermined region and a color Doppler scan in relation to the predetermined region.

9. The ultrasonic diagnostic apparatus according to claim 1, wherein
the processing circuitry is configured to alternately perform a B-mode scan in relation to a part of the predetermined region and a color Doppler scan in relation to the predetermined region, and implement a B-mode scan in relation to the predetermined region using data obtained by the B-mode scan over a plurality of frames.

10. An ultrasonic image processing apparatus comprising:
a memory configured to store a plurality of reception signals acquired from ultrasonic transmission performed with a direction of the ultrasonic transmission changed over multiple transmission directions, the reception signals being acquired for a plurality of reception rasters, respectively, in response to the ultrasonic transmission in each of the multiple transmission directions, the reception rasters being allocated to a predetermined region of a subject; and
processing circuitry configured to
acquire power information of a moving object in the predetermined region by
calculating a first signal for each of the reception rasters, wherein the first signal is calculated by adding together the reception signals that have been acquired for a respective one of the reception rasters in response to the ultrasonic transmission in the multiple transmission directions for a predetermined period,
calculating a second signal for each of the reception rasters, wherein the second signal is calculated by subjecting the first signal for the respective one of the reception rasters to first moving target indicator (MTI) filtering, and
calculating the power information based on the second signal,
acquire velocity information of the moving object by
calculating a third signal for each of the reception rasters, wherein the third signal is calculated by subjecting, to second MTI filtering, the reception signals that have been acquired for a respective one of the reception rasters in response to the ultrasonic transmission in the multiple transmission directions for the predetermined period and for a plurality of past periods consecutively preceding the predetermined period, and
calculating the velocity information based on the third signal, and
generate a Doppler image corresponding to the predetermined region based on the power information and the velocity information.

11. The ultrasonic image processing apparatus according to claim 10, wherein
the predetermined period and the past periods each correspond to one frame, the multiple transmission directions differ from each other by one reception raster width, and the reception signals are acquired while shifting a transmission position by a distance of the one reception raster width upon performing the ultrasonic transmission in each of the multiple transmission directions during the predetermined period and the past periods.

12. The ultrasonic image processing apparatus according to claim 11, wherein
the reception signals are acquired while shifting transmission positions.

13. The ultrasonic image processing apparatus according to claim 10, wherein the second MTI filtering comprises
approximating clutter with an eigenvalue and an eigenvector of a correlation matrix or a covariance matrix of the reception signals that have been acquired for the respective one of the reception rasters for the predetermined period and the past periods, and
subtracting the clutter from the reception signals that have been acquired for the respective one of the reception rasters for the predetermined period.

14. The ultrasonic image processing apparatus according to claim 10, wherein the second MTI filtering comprises
approximating clutter with polynomial fitting of the reception signals that have been acquired for the respective one of the reception rasters for the predetermined period and the past periods, and
subtracting the clutter from the reception signals that have been acquired for the respective one of the reception rasters for the predetermined period.

15. The ultrasonic image processing apparatus according to claim 10, wherein
the processing circuitry is configured to estimate velocity of the moving object in the predetermined region using an interval between a pulse pair having a predetermined data interval among the third signal.

16. The ultrasonic image processing apparatus according to claim 10, wherein the first MTI filtering comprises
approximating clutter with an eigenvalue and an eigenvector of a correlation matrix or a covariance matrix of the first signal calculated for the predetermined period and first signals calculated for the past periods for a corresponding, respective one of the reception rasters, and
subtracting the clutter from the first signal calculated for the predetermined period.

17. The ultrasonic image processing apparatus according to claim 10, wherein
the processing circuitry is configured to alternately perform a B-mode scan in relation to the predetermined region and a color Doppler scan in relation to the predetermined region.

18. The ultrasonic image processing apparatus according to claim 10, wherein
the processing circuitry is configured to perform a B-mode scan over a plurality of frames by alternately performing a B-mode scan in relation to a part of the predetermined region and a color Doppler scan in relation to the predetermined region.

19. An ultrasonic diagnostic apparatus control method comprising:

performing ultrasonic transmission while changing a direction of the ultrasonic transmission over multiple transmission directions;

acquiring, in response to the ultrasonic transmission in each of the multiple transmission directions, a plurality of reception signals for a plurality of reception rasters, respectively, wherein the reception rasters are allocated to a predetermined region of a subject;

acquiring power information of a moving object in the predetermined region by calculating a first signal for each of the reception rasters, wherein the first signal is calculated by adding together the reception signals that have been acquired for a respective one of the reception rasters in response to the ultrasonic transmission in the multiple transmission directions for a predetermined period, calculating a second signal for each of the reception rasters, wherein the second signal is calculated by subjecting the first signal for the respective one of the reception rasters to first moving target indicator (MTI) filtering, and calculating the power information based on the second signal;

acquiring velocity information of the moving object by calculating a third signal for each of the reception rasters, wherein the third signal is calculated by subjecting, to second MTI filtering, the reception signals that have been acquired for a respective one of the reception rasters in response to the ultrasonic transmission in the multiple transmission directions for the predetermined period and for a plurality of past periods consecutively preceding the predetermined period, and calculating the velocity information based on the third signal; and generating a Doppler image corresponding to the predetermined region based on the power information and the velocity information.

\* \* \* \* \*